US009112142B2

(12) United States Patent
Nakazawa et al.

(10) Patent No.: US 9,112,142 B2
(45) Date of Patent: Aug. 18, 2015

(54) PIEZOELECTRIC SENSOR DEVICE, AND POLARIZATION METHOD OF PIEZOELECTRIC BODY OF PIEZOELECTRIC SENSOR DEVICE

(75) Inventors: Yusuke Nakazawa, Nagano (JP); Tomohide Onogi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 499 days.

(21) Appl. No.: 13/495,146

(22) Filed: Jun. 13, 2012

(65) Prior Publication Data
US 2012/0323514 A1 Dec. 20, 2012

(30) Foreign Application Priority Data

Jun. 15, 2011 (JP) ................................. 2011-132885

(51) Int. Cl.
H01L 41/22 (2013.01)
H01L 41/113 (2006.01)
G01B 17/00 (2006.01)
G01S 7/52 (2006.01)
G01S 7/521 (2006.01)
G01S 7/523 (2006.01)
(Continued)

(52) U.S. Cl.
CPC ............ H01L 41/1132 (2013.01); G01B 17/00 (2013.01); G01S 7/521 (2013.01); G01S 7/523 (2013.01); G01S 7/52004 (2013.01); H01L 27/20 (2013.01); H01L 41/257 (2013.01); A61B 8/4483 (2013.01); A61B 8/58 (2013.01); Y10T 29/42 (2015.01)

(58) Field of Classification Search
CPC ... H01L 41/1132; H01L 41/22; H01L 41/253; H01L 41/257; H01L 27/20; G01S 7/523; G01S 7/521; G01S 7/52004; G01B 17/00; A61B 8/4483; A61B 8/58; H02N 2/008; H03H 2009/02196
USPC ....................... 702/57, 171; 73/632, 641, 649
See application file for complete search history.

(56) References Cited

U.S. PATENT DOCUMENTS 6,403,012 B1 * 6/2002 Tomohiro et al. ............. 264/406
8,324,784 B2 * 12/2012 Engel et al. ................... 310/319
(Continued)

FOREIGN PATENT DOCUMENTS

JP 2004-230033 A 8/2004
JP 2008-196926 A 8/2008
(Continued)

Primary Examiner — Manuel L Barbee
(74) Attorney, Agent, or Firm — Global IP Counselors, LLP

(57) ABSTRACT

A piezoelectric sensor device includes a piezoelectric element, a polarization processing unit and a controller. The piezoelectric element has a pair of electrodes sandwiching a piezoelectric body. The polarization processing unit is configured to execute polarization processing in which polarization voltage is applied to the polarization element. The controller is configured to control an execution timing of the polarization processing by the polarization processing unit, and includes a characteristics value acquisition unit configured to acquire a characteristics value relating to a polarization volume of the piezoelectric body, a determination unit configured to determine whether a polarization property is in a stable state or in an unstable state based on the characteristics value, and a polarization controller configured to control the polarization processing unit to apply the polarization voltage to the piezoelectric body when the determination unit determines that the polarization property of the piezoelectric body is in the unstable state.

11 Claims, 7 Drawing Sheets

(51) Int. Cl.
  *H01L 27/20* (2006.01)
  *H01L 41/257* (2013.01)
  *A61B 8/00* (2006.01)

(56) References Cited

U.S. PATENT DOCUMENTS

| | | |
|---|---|---|
| 2004/0260181 A1 | 12/2004 | Makita et al. |
| 2008/0030102 A1 | 2/2008 | Ohnishi et al. |
| 2008/0034873 A1 | 2/2008 | Habu et al. |
| 2008/0098582 A1 | 5/2008 | Ohnishi et al. |
| 2008/0111453 A1 | 5/2008 | Yoshioka et al. |
| 2009/0174419 A1 | 7/2009 | Ohnishi et al. |
| 2010/0043190 A1 | 2/2010 | Habu et al. |
| 2010/0064806 A1 | 3/2010 | Inaguma |

FOREIGN PATENT DOCUMENTS

| | | |
|---|---|---|
| JP | 2010-071758 A | 4/2010 |
| JP | 2010-252839 A | 11/2010 |
| JP | 2011-180403 A | 9/2011 |
| WO | 2007/001044 A1 | 1/2007 |
| WO | WO-2008/018278 A1 | 2/2008 |

* cited by examiner

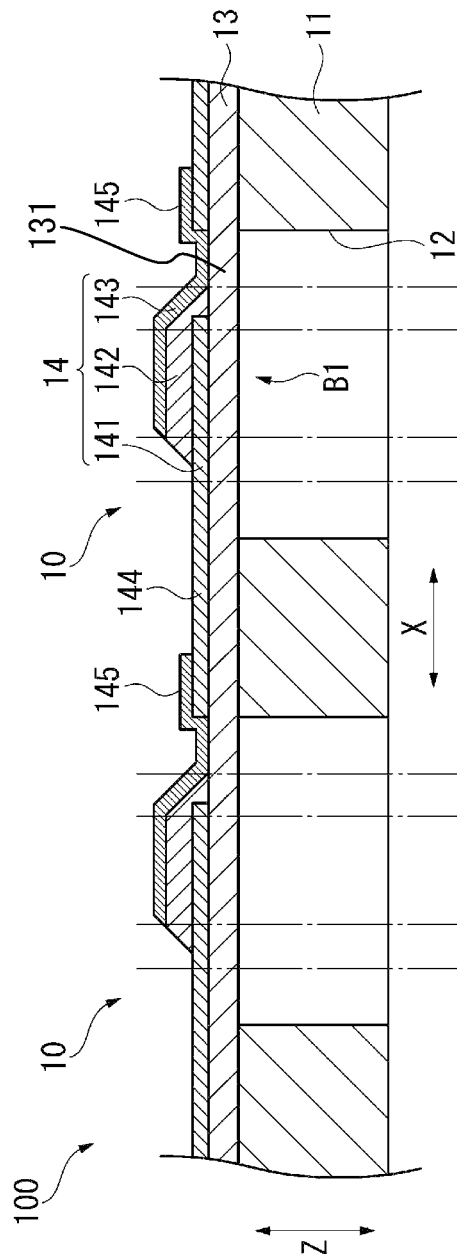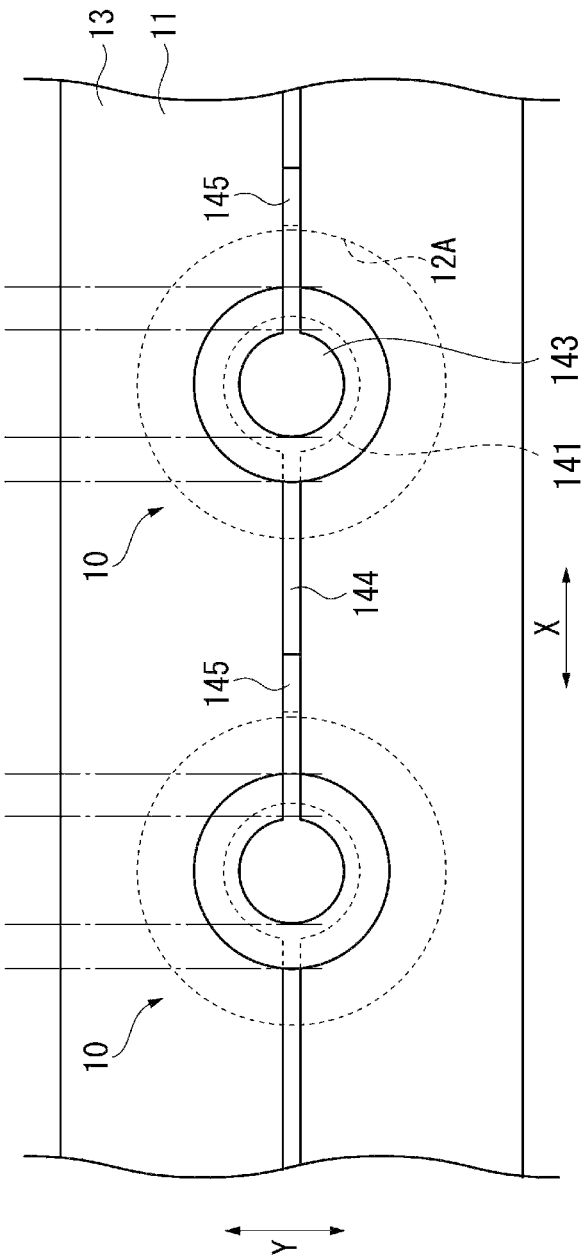
Fig. 2A
Fig. 2B

PIEZOELECTRIC SENSOR DEVICE, AND POLARIZATION METHOD OF PIEZOELECTRIC BODY OF PIEZOELECTRIC SENSOR DEVICE

CROSS-REFERENCE TO RELATED APPLICATIONS

This application claims priority to Japanese Patent Application No. 2011-132885 filed on Jun. 15, 2011. The entire disclosure of Japanese Patent Application No. 2011-132885 is hereby incorporated herein by reference.

BACKGROUND

1. Technical Field

The present invention relates to a piezoelectric sensor device and a polarization method of a piezoelectric body of a piezoelectric sensor device.

2. Related Art

Piezoelectric sensor devices equipped with a piezoelectric body have been known from the past (e.g., see International Patent Publication No. 2008/018278).

The ultrasonic probe (piezoelectric sensor device) noted in the above mentioned publication has a configuration whereby a piezoelectric layer for transmitting, an electrode layer, and a piezoelectric layer for receiving are laminated in sequence. This kind of ultrasonic probe has the electrode layer formed on the piezoelectric layer for transmitting, and that piezoelectric layer for transmitting undergoes polarization processing. After that, the piezoelectric layer for receiving is laminated on the electrode layer, a peelable dielectric layer is further laminated on the piezoelectric layer for receiving, the piezoelectric layer for receiving undergoes polarization processing, the dielectric layer is peeled after polarization processing of that piezoelectric layer for receiving, thus producing the ultrasonic probe.

SUMMARY

However, with the ultrasonic probe noted in the above mentioned publication, polarization processing of the piezoelectric bodies (piezoelectric layer for transmitting and piezoelectric layer for receiving) is performed only during production, and after that, the dielectric layer for polarization processing is peeled.

However, with the effects of residual stress due to accumulated vibration, static electricity and the like on the piezoelectric body, there is the problem that its piezoelectric properties may degrade over time. Specifically, when a set time has elapsed after polarization processing, the piezoelectric body is in a stable state for which there are almost no changes in polarization direction as time passes. However, after this stable state has been reached, when a prescribed time elapses, variations occur in the polarization direction, resulting in an unstable state. Therefore, for example, when ultrasonic waves are received by the piezoelectric sensor device, when in a stable state, good receiving sensitivity can be maintained, but when in an unstable state, there is the problem that receiving sensitivity becomes markedly worse.

An object of the present invention is to provide a piezoelectric sensor device and a polarization method of a piezoelectric body of a piezoelectric sensor device capable of inhibiting the degradation over time of the piezoelectric body.

A piezoelectric sensor device according to one aspect of the present invention includes a piezoelectric element, a polarization processing unit and a controller. The piezoelectric element has a piezoelectric body and a pair of electrodes sandwiching the piezoelectric body. The polarization processing unit is configured to execute polarization processing in which polarization voltage is applied to the polarization element. The controller is configured to control an execution timing of the polarization processing by the polarization processing unit. The controller includes a characteristics value acquisition unit, a determination unit, and a polarization controller. The characteristics value acquisition unit is configured to acquire a characteristics value relating to a polarization volume of the piezoelectric body. The determination unit is configured to determine whether a polarization property of the piezoelectric body is in a stable state or in an unstable state based on the characteristics value. The polarization controller is configured to control the polarization processing unit to apply the polarization voltage to the piezoelectric body when the determination unit determines that the polarization property of the piezoelectric body is in the unstable state.

With the above described aspect of the present invention, the execution timing of the polarization processing by which polarization processing is executed on the piezoelectric body that the piezoelectric element has is controlled as noted below by the characteristics value acquisition unit, the determination unit, and the polarization controller that constitute the controller. Specifically, the determination unit determines whether the polarization properties of the piezoelectric body are in a stable state or an unstable state based on the characteristics values according to the polarization volume of the piezoelectric body acquired by the characteristics value acquisition unit. Then, the polarization controller has polarization processing of the piezoelectric body done by the polarization processing unit when it is determined that the polarization properties of the piezoelectric body are in an unstable state based on the determination results of the determination unit. Because of that, even in a case when the polarization properties of the piezoelectric body degrade over time due to residual stress and static electricity or the like, and the polarization properties of the piezoelectric body are in an unstable state, since the piezoelectric body undergoes polarization processing, it is possible to return the piezoelectric body polarization properties to their pre-degradation state, making it possible to prevent a decrease in performance of the piezoelectric sensor device.

Also, for example when it is determined that the polarization properties of the piezoelectric body are in a stable state, by having it so that the piezoelectric body does not undergo polarization processing, it is possible to maintain the stable state of the piezoelectric body polarization properties while also decreasing unnecessary polarization processing and reducing power consumption.

With the above described aspect of the piezoelectric sensor device of the present invention, the characteristics value acquisition unit preferably includes a clock unit configured to acquire as the characteristics value an elapsed time from an execution timing of the polarization processing by the polarization processing unit, and the determination unit is preferably configured to determine that the polarization property of the piezoelectric body is in the stable state when the elapsed time falls between a first time and a second time, over which the polarization property of the piezoelectric body stabilizes, and to determine that the polarization property of the piezoelectric body is in the unstable state when the elapsed time is greater than the second time.

With the above described aspect of the present invention, with the elapsed time from the execution timing of the polarization processing as the characteristics value, when the elapsed time is the period from the first time which is the time for which the piezoelectric polarization properties are stable until the second time, this is determined to be a stable state, and when the elapsed time is greater than the second time, it is determined to be an unstable state.

Specifically, after polarization processing is executed on the piezoelectric body, changes in the polarization direction occur until a prescribed first time, resulting in an unstable state. Also, changes in the polarization direction are slow in the period from the first time to the second time, so a relatively stable polarization state is maintained. Then, from the second time and thereafter, the polarization direction rapidly becomes disordered, and the polarization state becomes unstable.

In contrast to this, with the above described aspect of the present invention, as described above, it is possible do polarization processing of the piezoelectric body at the timing when the stable state period has elapsed and the polarization properties of the piezoelectric body have degraded, so it is possible to effectively do polarization processing of the piezoelectric body. Also, because the elapsed time from the execution timing of the polarization processing is used as the characteristics value, it is easy to determine whether this is in a stable state or an unstable state.

It is preferable that the piezoelectric sensor device of the above described aspect of the present invention be equipped with a signal processing unit configured to execute at least one of detection processing for detecting a detection signal output from the piezoelectric element and drive processing for inputting a drive signal to the piezoelectric element to drive the piezoelectric element. The controller is preferably configured to stop the polarization processing of the piezoelectric body by the polarization processing unit and signal processing by the signal processing unit when the elapsed time is smaller than the first time.

As described above, until a prescribed first time has elapsed after polarization processing is executed, the change in the polarization direction of the piezoelectric body is great, resulting in an unstable state. In this unstable state, when signal processing is executed by the signal processing unit, for example when drive processing is performed to drive the piezoelectric element as the signal processing, the drive volume of the piezoelectric element changes according to the drive timing. Also, when detection processing for detecting displacement volume of the piezoelectric element is performed as the signal processing, because the receiving sensitivity fluctuates, it is not possible to do accurate detection of the displacement volume of the piezoelectric element.

In contrast to this, with the above described aspect of the present invention, when the elapsed time is smaller than the first time, signal processing by the signal processing unit is stopped, and signal processing is not executed. By doing this, it is possible to inhibit a decrease in signal processing precision due to fluctuations in the receiving operation of the piezoelectric element.

Also, in the unstable state until the first time after execution of the polarization processing, when polarization processing is performed, the piezoelectric body polarization state again becomes unstable until elapsing of the first time from the execution timing of this polarization processing. In contrast to this, with the present invention, until the first time after execution of the polarization processing, polarization processing of the piezoelectric body by the polarization processing unit is stopped, specifically, polarization processing is not executed, so it is possible to have the piezoelectric body go to a stable state quickly.

With the piezoelectric sensor device of the above described aspect of the present invention, the piezoelectric element is preferably configured to output a detection signal according to received ultrasonic waves. The piezoelectric sensor device preferably further includes a signal processing unit configured to detect a detection signal output from the piezoelectric element; a reference piezoelectric element constituted using the same structural materials as the piezoelectric element and formed with the same shape and dimensions thereof, and configured to output a reference signal according to the received ultrasonic waves; and a reference signal detection unit configured to detect the reference signal output from the reference piezoelectric element. The characteristics value acquisition unit preferably includes a differential value calculating unit configured to calculate as the characteristics value a differential value between the detection signal detected by the signal processing unit and the reference signal detected by the reference signal detection unit. The determination unit is preferably configured to determine that the polarization property of the piezoelectric body is in the stable state when the differential value calculated by the differential value calculating unit is a prescribed threshold or less, and to determine that polarization property of the piezoelectric body is in the unstable state when the differential value is greater than the prescribed threshold.

With the above described aspect of the present invention, the signal processing unit detects the detection signals according to the ultrasonic waves output by the piezoelectric element. Also, the reference signal detection unit detects reference signals according to ultrasonic waves output by a reference piezoelectric element constituted with the same constitutional materials as the concerned piezoelectric element, and is formed in the same shape and dimensions. Then, the characteristics value acquisition unit calculates as the characteristics value the differential value between the detection signals and reference signals, the determination unit determines there to be a stable state when the calculated differential value is a prescribed threshold value or less, and determines that there is an unstable state when the differential value is greater than the threshold value.

Here, the reference piezoelectric element is an element used to determine whether the piezoelectric element is in a stable state or an unstable state, and during normal signal processing, driving is stopped, and the polarization state is always kept in a stable state. Therefore, by comparing the strength of the received signals between this kind of reference piezoelectric element and the piezoelectric element, it is possible to judge the degradation state of the piezoelectric element, and to perform accurate determinations.

It is preferable that the piezoelectric sensor device of the above described aspect of the present invention be equipped with a mode switching unit configured to switch between a signal processing mode in which at least one of signal transmission processing and signal receiving processing of ultrasonic waves from the piezoelectric element is executed, and a calibration mode in which the polarization processing of the piezoelectric element is executed. The polarization controller is preferably configured to control the polarization processing unit to execute the polarization processing of the reference piezoelectric element in the signal processing mode.

Here, if the polarization processing of the reference piezoelectric element is when in the signal processing mode, execution can be done with any timing, with examples including the timing when the power is turned on to that piezoelectric sensor device, the timing when shifting to standby time without executing the detection processing of the detection signals by the signal processing unit for a specified time or greater, or any timing that is set by input by a user.

With the above described aspect of the present invention, the reference piezoelectric element has polarization processing done by the polarization processing unit when set to the signal processing mode by the mode switching unit. Therefore, when switched to the calibration mode by the mode switching unit, and determining whether the piezoelectric element polarization state is an unstable state or not, it is possible to compare accurate reference signals output from the reference piezoelectric element which has been set to a stable polarization state by polarization processing with detection signals of the piezoelectric element, making it possible to accurately determine the polarization state of the piezoelectric element.

A polarization method according to another aspect of the present invention is a method for polarizing a piezoelectric body of a piezoelectric sensor device including a piezoelectric element having a piezoelectric body and a pair of electrodes sandwiching the piezoelectric body, and a polarization processing unit configured to execute polarization processing in which polarizing voltage is applied to the piezoelectric element. The polarization method comprising: acquiring a characteristics value relating to a polarization volume of the piezoelectric body; determining whether a polarization property of the piezoelectric body is in a stable state or in an unstable state based on the characteristics value; and controlling the polarization processing unit to execute the polarization processing of the piezoelectric body when the polarization property of the piezoelectric body is determined to be in the unstable state.

With the above described aspect of the present invention, the execution timing for executing polarization processing on the piezoelectric body which the piezoelectric element has is controlled as follows by the characteristics value acquisition step, the determination step, and the polarization control step. Specifically, the determination step determines whether the polarization properties of the piezoelectric body are in a stable state or unstable state based on the characteristics value according to the polarization volume of the piezoelectric body acquired with the characteristics value acquisition step. Then, with the polarization control step, when it is determined that the polarization properties of the piezoelectric body are in an unstable state based on the determination results of this determination step, the piezoelectric body undergoes polarization processing by the polarization processing unit. Because of this, even when there is degradation over time of the piezoelectric body polarization properties due to residual stress, static electricity or the like, and the piezoelectric body polarization properties are in an unstable state, the piezoelectric body undergoes polarization processing, so it is possible to return the piezoelectric body polarization properties to the pre-degradation state, making it possible to prevent a decrease in performance of the piezoelectric sensor device.

Also, for example, when it is determined that the piezoelectric body polarization properties are in a stable state, by having polarization processing of the piezoelectric body not performed, while maintaining a stable state of the piezoelectric body polarization properties, it is possible to decrease unnecessary polarization processing and to reduce power consumption.

BRIEF DESCRIPTION OF THE DRAWINGS

Referring now to the attached drawings which form a part of this original disclosure:

FIGS. 2A and 2B are diagrams showing the configuration of the receiving element of the first embodiment.

DETAILED DESCRIPTION OF EXEMPLARY EMBODIMENTS

First Embodiment

Figure 1:
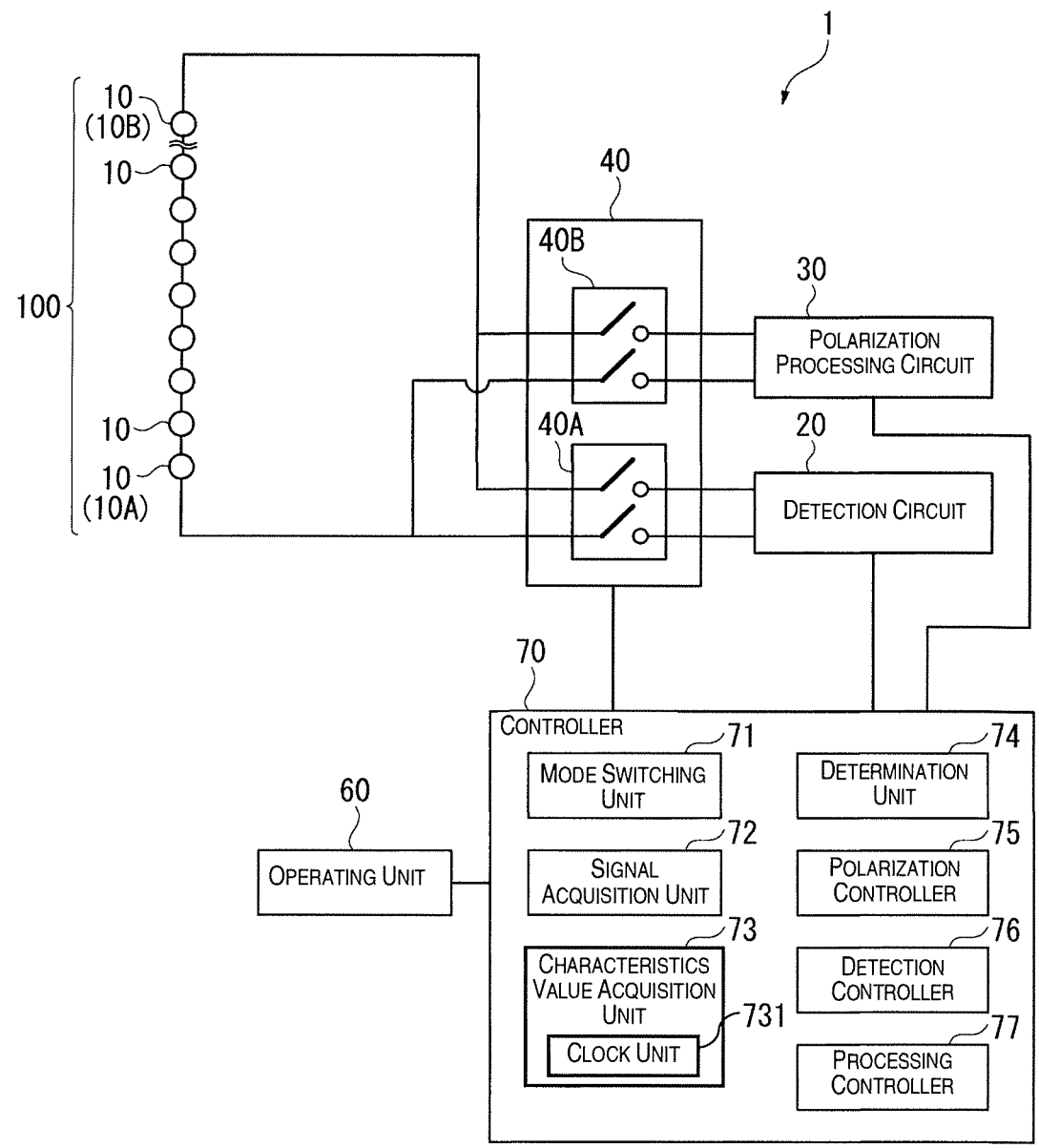
FIG. 1 is a diagram showing the configuration of the ultrasonic sensor of a first embodiment of the present invention.

Following, we will describe a first embodiment of the present invention while referring to the drawings.

Schematic Configuration of Ultrasonic Sensor

FIG. 1 is a diagram showing the configuration of an ultrasonic sensor 1 as the piezoelectric sensor device. This ultrasonic sensor 1 is a sensor for detecting the distance between the ultrasonic sensor 1 and the object to be detected as well as the state of the object to be detected by receiving ultrasonic waves reflected by the object to be detected that were sent to the object to be detected. This kind of ultrasonic sensor 1 can be used for various kinds of devices that send or receive ultrasonic waves, such as a biopsy device for measuring in vivo blood vessel position, blood flow speed, blood pressure and the like, for example, by sending and receiving ultrasonic waves, a stress measuring device for measuring pressing force or sheer force acting on an elastic film by detecting through use of ultrasonic waves the movement of the elastic film provided on the surface to the ultrasonic sensor 1, an ultrasonic cleaning device that uses ultrasonic waves to measure the distance from a target object and cleans that target object with sound pressure according to the measured distance, or the like.

As shown in FIG. 1, this ultrasonic sensor 1 is equipped with a plurality of receiving elements 10 (piezoelectric elements), a detection circuit 20 (signal processing unit) for detecting detection signals output from the receiving element 10, a polarization processing circuit 30 (polarization processing unit), a connection switching circuit 40 (connection switching unit), a power supply unit (not shown), an operating unit 60, and a controller 70.

Configuration of Receiving Element

FIG. 2 is a diagram showing the schematic configuration of the receiving element 10. In specific terms, FIG. 2 (A) is a cross section view of the receiving element 10, and FIG. 2 (B) is a plan view of the receiving element 10.

The receiving element 10 is an element that receives ultrasonic waves and converts them to detection signals.

A plurality of these receiving elements 10 are arranged at equal intervals on a support unit 11 along the axial directions of the respective X axis and Y axis which are orthogonal to each other, and a receiving element group 100 with an array configuration is constituted by this plurality of receiving elements 10.

As shown in FIG. 2, each receiving element 10 is equipped with a support unit 11 on which an opening 12 is formed, a support film 13 which covers the support unit 11 and blocks the opening 12, and a laminated body 14 formed on the support film 13.

The opening 12 formed on the support unit 11 is formed, for example, in the circular shape seen with the plan view as shown in FIG. 2 (B). As a result, at a diaphragm 131 which is the support film 13 on the inside of the opening 12, it is possible to make the stress in relation to the deflection of the diaphragm 131 uniform.

Film formation of the support film 13 is done on the support unit 11 in a state with the opening 12 blocked. This support film 13 is constituted using a two-layer constitution of an $SiO_2$ layer and a $ZrO_2$ layer, for example. Here, when the support unit 11 is an Si substrate, film formation of the $SiO_2$ layer can be done by doing thermal oxidation processing of the substrate surface. Also, film formation of the $ZrO_2$ layer can be done using a method such as sputtering or the like on the $SiO_2$ layer, for example. Here, the $ZrO_2$ layer is a layer for preventing diffusion of Pb, which constitutes PZT, into the $SiO_2$ layer when using PZT as the piezoelectric film 142 described later, for example. The $ZrO_2$ film also has effects such as increasing the deflection efficiency in relation to distortion of the piezoelectric film 142.

The laminated body 14 is equipped with a lower electrode 141 laminated on the top layer of the support film 13, a piezoelectric film 142 as the piezoelectric body formed on the lower electrode 141, and an upper electrode 143 formed on the piezoelectric film 142. In other words, the laminated body 14 has a constitution with which the piezoelectric film 142 is sandwiched by a pair of electrodes (lower electrode 141 and upper electrode 143).

Also, as shown in FIG. 2, on the lower electrode 141, a lower electrode wire 144 is drawn along the support film 13. Also, on the upper electrode 143, an upper electrode wire 145 is drawn facing opposite the drawing direction of the lower electrode wire 144 along the support film 13. Then, with a planar view, the lower electrode wire 144 is overlapping the upper electrode wire 145 of the receiving element 10 that is arranged adjacently. In this way, the receiving elements 10 are serially connected as shown in FIG. 1 by having the lower electrode wire 144 and the upper electrode wire 145 of each receiving element 10 overlap for connection.

With this kind of receiving element group 100, by a plurality of receiving elements 10 being serially connected, the detection signals output from the receiving elements 10 are added together, so it is possible to output detection signals with a large signal value to the detection circuit 20.

Though not shown in detail, with this embodiment, we showed an example of a sensor configuration whereby, of the plurality of receiving elements 10, only the element groups arranged in the X axis direction are connected serially to constitute the receiving element group 100, such receiving element groups 100 are provided in parallel along the Y axis, and each of the receiving element groups 100 are connected individually to the detection circuit 20, but the invention is not restricted thereto. For example, by the receiving elements 10 arranged at one end in the X axis direction being serially connected with the receiving elements 10 adjacent in the Y axis direction, it is also possible to have a configuration for which the receiving elements 10 arranged in the X axis direction and the Y axis direction are serially connected.

The piezoelectric film 142 is formed by doing film formation of, for example, PZT (lead zirconate titanate) in film form. With this embodiment, PZT is used as the piezoelectric film 142, but any material can be used as long as it is a material that can be contracted in the inner surface direction by applying voltage, for example lead titanate ($PbTiO_3$), lead zirconate ($PbZrO_3$), lead lanthanum titanate (($Pb$, $La)TiO_3$) or the like may also be used.

With such a receiving element 10, by ultrasonic waves being received at the diaphragm 131, the diaphragm 131 vibrates in the film thickness direction (Z axis direction in FIG. 2 (A)). As a result, potential difference is generated at the surface of the lower electrode 141 side and the surface of the upper electrode 143 side of the piezoelectric film 142, and a detection signal (current) is output from the upper electrode 143 and the lower electrode 141 according to the displacement volume of the piezoelectric film 142.

Configuration of Detection Circuit

The detection circuit 20 shown in FIG. 1 is a circuit that executes detection processing for detecting (acquiring) detection signals output from each receiving element 10, and is connected to the previously described receiving element group 100 via the connection switching circuit 40. More specifically, the detection circuit 20 is connected to the lower electrode wire 144 of the receiving elements 10 (receiving elements 10A) arranged at one end of the receiving element group 100 and to the upper electrode wire 145 of the receiving elements 10 (receiving element 10B) arranged at the other end of the receiving element group 100. Then, this detection circuit 20 amplifies the voltage value of the detection signal input from the receiving element group 100 and outputs it to the controller 70.

Configuration of Polarization Processing Circuit

The polarization processing circuit 30 is equipped with a voltage source capable of outputting a polarization voltage for performing polarization processing on the previously described piezoelectric film 142, and is connected to the receiving element group 100 via the connection switching circuit 40. By this polarization processing circuit 30 applying the polarization voltage to the receiving element group 100, divided voltage of the concerned polarization voltage is applied to the piezoelectric film 142 of each receiving element 10. Note that the applied voltage and time may be executed at preset values according to the characteristics of the piezoelectric film 142, for example.

Configuration of Connection Switching Circuit

The connection switching circuit 40 is constituted using a switching element such as a (TFT (Thin Film Transistor)) or the like, for example, and is equipped with a first switch unit 40A provided between the receiving element group 100 and the detection circuit 20, and a second switch unit 40B provided between the receiving element group 100 and the polarization processing circuit 30. Then, the first switch unit 40A switches the connection state of the receiving element group 100 and the detection circuit 20 by the control of the controller 70. Also, the second switch unit 40B switches the connection state of the receiving element group 100 and the polarization processing circuit 30 by the control of the controller 70.

Here, a state with the receiving element group 100 and the detection circuit 20 connected by the first switch unit 40A, and the receiving element group 100 and the polarization processing circuit 30 disconnected by the second switch unit 40B is the first connection state of the present invention. Also, a state with the receiving element group 100 and the detection circuit 20 disconnected by the first switch unit 40A, and the receiving element group 100 and the polarization processing circuit 30 connected by the second switch unit 40B is the second connection state of the present invention. Also, a state for which both the first switch unit 40A and the second switch unit 40B are disconnected, specifically, a state for which the receiving element group 100 and the detection circuit 20 are disconnected, and the receiving element group 100 and the polarization processing circuit 30 are disconnected is the third connection state.

Configuration of Operating Unit

The operating unit 60 is provided on an external part of the ultrasonic sensor 1 that is not shown, and is a part with which input signals are input by the operation of a user. As this operating unit 60, for example, though not shown, examples include a power switch by which the ultrasonic sensor 1 is activated by power from the power supply unit, a processing start button that executes receiving processing of ultrasonic waves (transmission and receiving processing) or the like.

Configuration of Controller

The controller 70 is connected to the previously described detection circuit 20, the polarization processing circuit 30, the connection switching circuit 40, and the operating unit 60, and controls the timing of executing polarization processing using the polarization processing circuit (execution timing of the polarization processing).

This controller 70 is constituted from an integrated circuit such as an IC (Integrated Circuit) or the like for example, and does overall control of the ultrasonic sensor 1. In specific terms, as shown in FIG. 1, the controller 70 is constituted equipped with a mode switching unit 71, a signal acquisition unit 72, a characteristics value acquisition unit 73, a determination unit 74, a polarization controller 75, a detection controller 76, and a processing restriction unit 77 and the like.

The mode switching unit 71 switches and sets the operating mode of the ultrasonic sensor 1. In specific terms, the mode switching unit 71 switches between the signal processing mode which allows detection by the detection circuit 20 of detection signals from the receiving element group 100, the calibration mode for which polarization processing of the receiving element group 100 is executed by the polarization processing circuit 30, and a stability transition mode for restricting both processing of detection processing by the detection circuit 20 and the polarization processing by the polarization processing circuit 30.

Switching of the operating mode of the ultrasonic sensor 1 by the mode switching unit 71 is executed based on the determination of the polarization state of the piezoelectric film 142 by the determination unit 74 described later.

The signal acquisition unit 72 acquires input signals that have been input from the operating unit 60. As described above, as these input signals, examples include input signals indicating that the power switch has been switched to the on state, input signals to the effect of starting detection processing of ultrasonic waves by the receiving element group 100, and the like.

The characteristics value acquisition unit 73 is equipped with a clock unit 731 that uses a timer (not shown) to measure the time that has elapsed from the execution timing of polarization processing by the polarization processing circuit 30.

Then, this characteristics value acquisition unit 73 acquires the elapsed time (t) timed by the clock unit 731 as the characteristics value according to the polarization volume of the piezoelectric film 142.

The determination unit 74 determines whether the polarization properties of the piezoelectric film 142 are in a stable state or an unstable state according to the elapsed time (t) acquired by the characteristics value unit 73.

Here, we will describe the relationship between this elapsed time (t) and the polarization state of the piezoelectric film 142.

Figure 3:
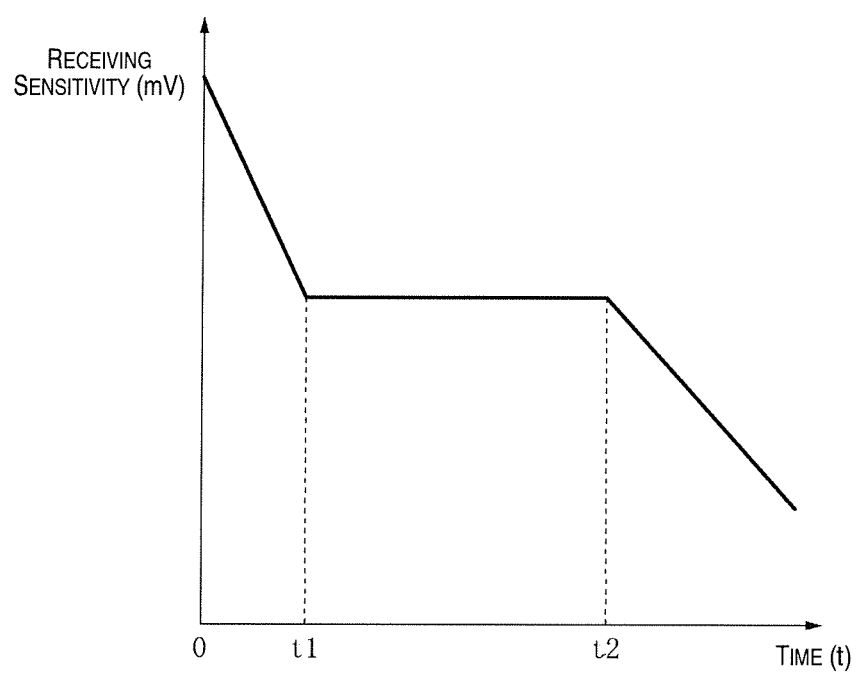
FIG. 3 is a graph showing the receiving sensitivity of the ultrasonic sensor of the first embodiment.

FIG. 3 is a graph showing the receiving sensitivity of the ultrasonic sensor 1. In FIG. 3, the horizontal axis indicates the elapsed time (t), and the vertical axis indicates the receiving sensitivity (mV) of the receiving elements 10.

When polarization processing is executed on the piezoelectric film 142, immediately after polarization processing (t=0), it is possible to orient the polarization direction for each domain in one direction. However, this state is unstable, so it is easy for the polarization direction of each domain to change, and after a prescribed time (first time: t=t1) has elapsed, this becomes a stable state for which the polarization direction changes are small. Then, after this stable state has continued for a prescribed time (t=t2), the piezoelectric film 142 again goes to an unstable state for which polarization direction changes occur easily. Note that this first time and second time are values that change according to the constitutional materials, crystal structure and the like of the piezoelectric film 142, and it is possible to know these by measuring in advance when forming the receiving elements 10, for example.

Because of this, with the receiving elements 10, as shown in FIG. 3, from after polarization processing until the first time ($0 \leq t < t1$), though the receiving sensitivity is high, the volume of change in the receiving sensitivity is also greater. Therefore, during this period, when detection processing is executed, the detection signal size changes due to differences in the detection timing even when ultrasonic waves of the same sound pressure are received.

Meanwhile, with the stable state of the period of from the first time to the second time ($t1 \leq t \leq t2$), changes in the polarization direction of the piezoelectric film 142 are small, so as shown in FIG. 3, the receiving elements 10 can maintain a constant receiving sensitivity. Therefore, when ultrasonic waves of the same sound pressure are received, even when the detection timing is different, detection signals of approximately the same signal are acquired.

Then, after the second time has elapsed (t>t2), as noted above, the polarization direction of the piezoelectric film 142 changes rapidly, so when detection processing is executed during this time, even when ultrasonic waves of the same sound pressure are received, changes in the detection signal size occur due to differences in the detection timing. Also, since the polarization direction is not uniform, the signal values of the detection signals output from the piezoelectric film 142 are also smaller, and as shown in FIG. 3, the receiving sensitivity of the receiving elements 10 also decreases.

The determination unit 74 determines that the polarization properties of the piezoelectric film 142 are in a stable state when the elapsed time (t) acquired by the characteristics value acquisition unit 73 is the time from the first time, which is the time for which the polarization properties of the piezoelectric film 142 are stable, until the second time. Furthermore, the determination unit 74 determines a stability transition state when the elapsed time (t) is the time from immediately after polarization processing until the first time.

When it is determined that the polarization properties of the piezoelectric film 142 are in an unstable state based on the determination results of this determination unit 74, and the operating mode of the ultrasonic sensor 1 is switched to the calibration mode by the mode switching unit 71, the polarization controller 75 outputs control signals to the connection switching circuit 40, switches the connection state of the connection switching circuit 40 to the second connection state, and has polarization processing of the piezoelectric film 142 done by the polarization processing circuit 30.

When it is determined that the polarization properties of the piezoelectric film 142 are in a stable state based on the determination results of this determination unit 74, and the operating mode of the ultrasonic sensor 1 is switched to the signal processing mode by the mode switching unit 71, the detection controller 76 outputs control signals to the connection switching circuit 40, and switches to the first connection state. Then, the detection signals output from the receiving element group 100 are detected by the detection circuit 20. The detection controller 76 may also calculate the distance from the ultrasonic sensor 1 to the object to be detected or the like based on the detected detection signals, or may output the detected detection signals to an external apparatus from an external terminal unit (not shown), for example.

When it is determined that the polarization properties of the piezoelectric film 142 are in a stability transition state based on the determination results of the determination unit 74, and the operating mode of the ultrasonic sensor 1 is switched to the stability transition mode by the mode switching unit 71, the processing restriction unit 77 outputs control signals to the connection switching circuit 40 and switches to the third connection state. As a result, the reception element group 100 is in a state whereby the detection circuit 20 and the polarization processing circuit 30 are disconnected, and the detection processing by the detection circuit 20 and the polarization processing by the polarization processing circuit 30 are restricted, specifically, are in a stopped state.

Configuration of Ultrasonic Sensor

Figure 4:
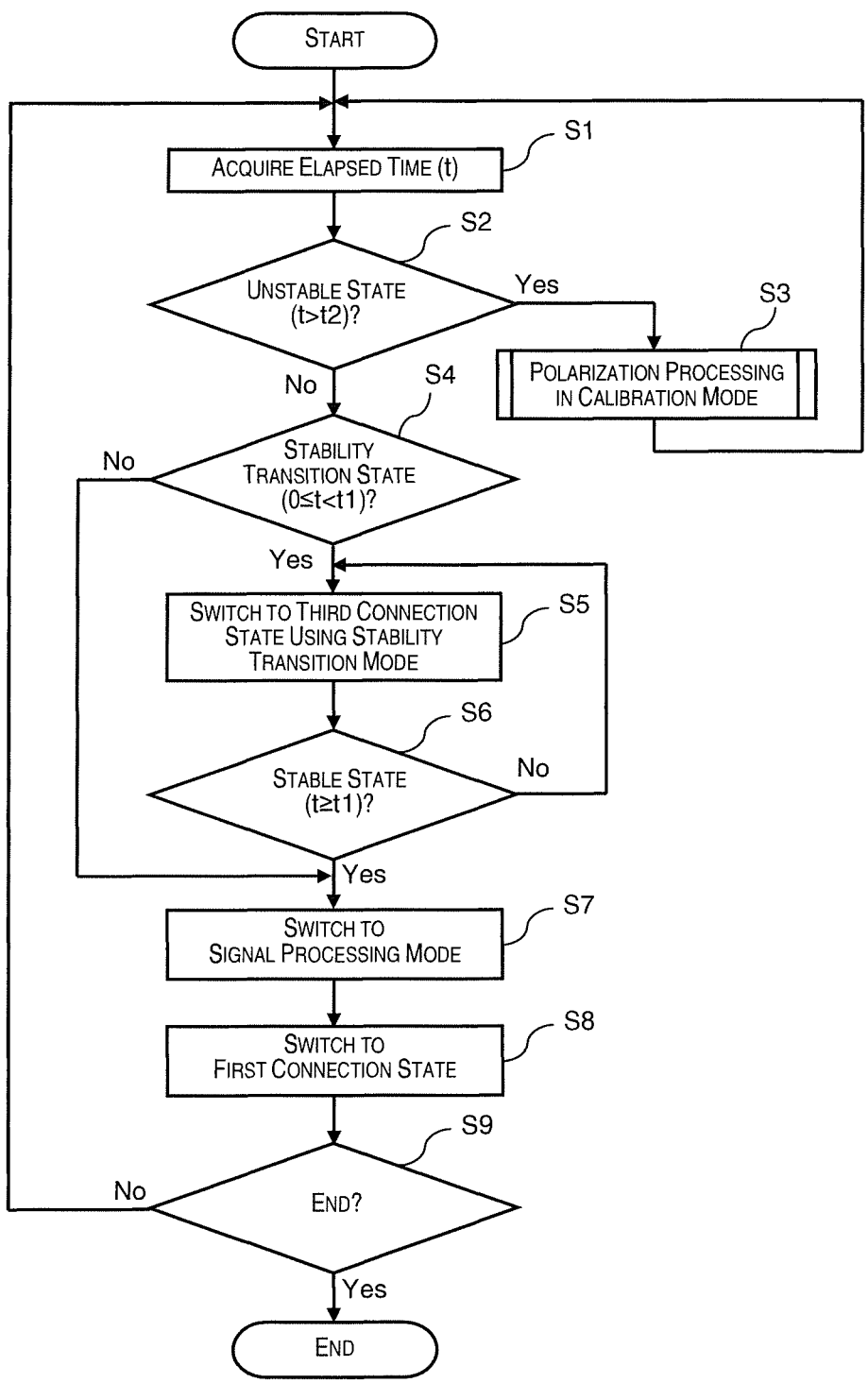
FIG. 4 is a flow chart showing the operation of the ultrasonic sensor of the first embodiment.

FIG. 4 is a flow chart showing the operation of the ultrasonic sensor 1.

When the power switch of the ultrasonic sensor 1 is turned on, the clock unit 731 of the characteristics value acquisition unit 73 acquires the elapsed time (t) from the timing when the previous polarization processing was executed by the internal timer of the controller 70 until the current time (step S1).

Next, the determination unit 74 of the controller 70 judges whether or not the polarization state of the piezoelectric film 142 is an unstable state or not based on the elapsed time (t) acquired at step S1 (step S2). Specifically, the determination unit 74 judges whether or not the elapsed time (t) is greater than the second time t2.

At this step S2, when it is determined by the determination unit 74 that there is an unstable state, the mode switching unit 71 switches the operating mode of the ultrasonic sensor 1 to the calibration mode, and polarization processing for polarizing the piezoelectric film 142 of each receiving element 10 of the receiving element group 100 is executed (step S3).

Figure 5:
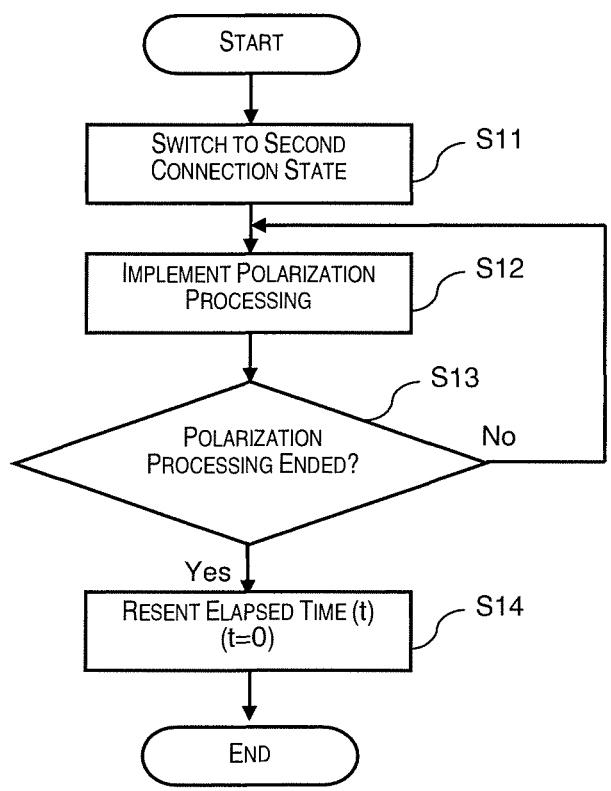
FIG. 5 is a flow chart of the polarization processing of the first embodiment.

FIG. 5 is a flow chart of the polarization processing.

With the polarization processing of step S3, the polarization controller 75 switches the connection state of the connection switching circuit 40 to the second state (step S11). Then, the polarization controller 75 has a polarization voltage applied to the piezoelectric film 142 of each receiving element 10 from the polarization processing circuit 30 to execute polarization processing to each piezoelectric film 142 (step S12).

Next, the polarization controller 75 determines whether the polarization processing of the piezoelectric film 142 has ended (step S13). This determination can be performed by timing the processing time using the timer, for example.

When it is determined at step S13 that the polarization processing has not ended, the polarization controller 75 maintains the second connection state, and executes the polarization processing until the polarization processing of each piezoelectric film 142 has ended.

When it is determined at step S13 that the polarization processing has ended, the characteristics value acquisition unit 73 resets (sets t=0) the elapsed time (t) measured by the clock unit 731 (step S14). With the above, the polarization processing of step S3 ends.

When this polarization processing by step S3 ends, the process returns to the processing of step S1.

Meanwhile, with the previously described processing of step S2, when the determination unit 74 determines that it is not in an unstable state, it further determines whether or not it is in a stability transition state for which the elapsed time (t) is $0 \le t < t1$ (step S4).

At this step S4, when it is determined by the determination unit 74 that this is in a stability transition state, the mode switching unit 71 switches the operating mode of the ultrasonic sensor 1 to the stability transition mode. For example, immediately after the polarization processing of step S3 is executed, this is determined to be a stability transition state.

Then, when the operating mode is switched to the stability transition mode by the mode switching unit 71, the processing restriction unit 77 switches the connection state of the connection switching circuit 40 to the third connection state (step S5).

At this step S5, the processing restriction unit 77 maintains the connection state of the connection switching circuit 40 at the third connection state until the elapsed time (t) measured by the clock unit 731 of the characteristics value acquisition unit 73 becomes $t \ge t1$, and restricts input and output of signals to the receiving element group 100. Specifically, the polarization processing by the polarization processing circuit 30 and the detection processing by the detection processing 20 are in a stopped state. As a result, detection of detection signals in an unstable state for which polarization properties of the receiving element 10 change easily is prevented. By stopping the polarization processing by the polarization processing circuit 30, it is possible to have the polarization properties of the receiving elements 10 transition smoothly to a stable state.

Then, the determination unit 74 determines whether the elapsed time (t) measured by the clock unit 731 is $t1 \le t \le t2$ or not, specifically, the determination unit 74 determines whether or not the polarization state of the receiving element group 100 is in a stable state (step S6). Here, when the elapsed time (t) is $t < t1$, as described previously, the processing of step S5 continues. Meanwhile, at step S6, when it is determined by the determination unit 74 that the elapsed time (t) is $t1 \le t \le t2$, and at step S4, when it is determined by the determination unit 74 that it is not in a stability transition state, the mode switching unit 71 switches the operating mode of the ultrasonic sensor 1 to the signal processing mode (step S7).

Then, when the operating mode of the ultrasonic sensor 1 is set to the signal processing mode by the mode switching unit 71, the detection controller 76 switches the connection state of the connection switching circuit 40 to the first connection state (step S8). Specifically, this is set to a state for which it is possible to receive ultrasonic waves by the receiving element group 100.

At this step S8, ultrasonic waves are issued from an ultrasonic wave transmitting element (not shown), and when the ultrasonic waves reflected by the object to be detected are received by each receiving element 10, the detection signals from the receiving element group 100 are output to the detection circuit 20. The detection circuit 20 amplifies the detection signals, and outputs them to the controller 70.

Then, the detection controller 76 calculates for example the distance from the ultrasonic sensor 2 to the object to be detected or the like based on the detection signals output from the detection circuit 20, and outputs that as the measurement results to an output device (not shown) or the like.

Then, the controller 70 determines whether or not to continue the detection processing (step S9), and when continuing, the process returns to step S1.

Meanwhile, when the detection processing is ended by the power switch being turned off or the like, operation ends.

With the ultrasonic sensor 1 of the first embodiment described above, the following effects are exhibited.

The ultrasonic sensor 1 is equipped with a polarization processing circuit 30 that applies a polarization voltage to the piezoelectric film 142 to execute polarization processing, and a controller 70 for controlling the execution timing of the polarization processing by the polarization processing circuit 30. Also, the controller 70 is equipped with the characteristics value acquisition unit 73 for acquiring characteristics values according to the polarization volume of the piezoelectric film 142, the determination unit 74 that determines whether the polarization properties of the piezoelectric film 142 are in a stable state or an unstable state based on those characteristics values, and a polarization controller 75 that has polarization processing of the piezoelectric film 142 done by the polarization processing circuit 30 when it is determined that the piezoelectric film 142 polarization properties are in an unstable state based on the determination results of the determination unit 74.

As a result, the execution timing of the polarization processing by which polarization processing is executed on the piezoelectric films 142 that each receiving element 10 has is controlled as follows by the characteristics value acquisition unit 73, the determination unit 74, and the polarization controller 75 that constitute the controller 70. Specifically, the determination unit 74 determines whether the piezoelectric film 142 polarization properties are in a stable state or an unstable state based on the characteristics values according to the polarization volume of the piezoelectric film 142 acquired by the characteristics value acquisition unit 73. Then, the polarization controller 75 has polarization processing of the piezoelectric film 142 done by the polarization processing circuit 30 when it is determined that the piezoelectric film 142 polarization properties are in an unstable state based on the determination results of this determination unit 74. Because of this, even in a case when the piezoelectric film 142 polarization properties degrade over time due to the effect of residual stress, static electricity or the like, and the piezoelectric film 142 polarization properties are in an unstable state, because the piezoelectric film 142 undergoes polarization processing, it is possible to return the piezoelectric film 142 polarization properties to their pre-degradation state, making it possible to prevent a decrease in performance of the ultrasonic sensor 1.

Also, when it is determined that the piezoelectric film 142 polarization properties are in a stable state, by making it so that polarization processing of the piezoelectric film 142 is not done, it is possible to maintain a stable state for the piezoelectric film 142 polarization properties while decreasing unnecessary polarization processing and reducing power consumption.

Also, with the elapsed time (t) from the polarization processing execution timing as the characteristics value, the characteristics value acquisition unit 73 determines that it is a stable state when the elapsed time (t) is the time from the first time, which is the time for which the piezoelectric film 142 polarization properties are stable, until the second time ($t1 \leq t \leq t2$), and determines that it is an unstable state when the elapsed time (t) is greater than the second time (t>2). As a result, it is possible do polarization processing of the piezoelectric film 142 at the timing for which the stable state period has elapsed and the polarization properties of the piezoelectric film 142 have degraded, so it is possible to effectively do polarization processing of the piezoelectric film 142. Also, since the elapsed time (t) from the polarization processing execution timing is used as the characteristics value, it is possible to easily determine whether this is a stable state or an unstable state.

Furthermore, with the ultrasonic sensor 1, a detection circuit 20 is equipped which detects detection signals output from the piezoelectric film 142, and when the elapsed time (t) is smaller than the first time ($0 \leq t < t1$), the controller 70 stops the polarization processing of the piezoelectric film 142 by the polarization processing circuit 30 and the signal processing (detection processing) by the detection circuit 20.

Here, in the period until a prescribed first time has elapsed after polarization processing is executed, the changes in the polarization direction of the piezoelectric film 142 are great, and this is an unstable state. In this unstable state, when signal processing (detection processing) is executed by the detection circuit 20, the receiving sensitivity fluctuates, so it is not possible to execute accurate piezoelectric film 142 displacement volume detection.

In contrast to this, with this embodiment, when the elapsed time (t) is smaller than the first time, the detection processing by the detection circuit 20 is stopped, and detection processing is not executed. As a result, it is possible to inhibit a decrease in signal processing precision due to fluctuation of the receiving sensitivity of the receiving elements 10.

Also, the period up to the first time after polarization processing has been executed is determined to be a stability transition state, and is not determined to be an unstable state. Specifically, when it is determined by the determination unit 74 that there is an unstable state, and polarization processing is executed by the polarization processing circuit 30, until another first time has elapsed from the timing of this polarization processing execution, the polarization state of the piezoelectric film 142 is again unstable. In contrast to this, with this embodiment, as noted above, the time until the first time after polarization processing has been executed is determined to be a stability transition state, and by restricting the polarization processing of the piezoelectric film 142 by the polarization processing circuit 30 and detection processing by the detection circuit 20, in other words, by stopping them, it is possible to put the polarization state of the piezoelectric film 142 to a stable state quickly.

Here, compared to an ultrasonic sensor constituted with a single element (one receiving element), an ultrasonic sensor equipped with a constitution for which a plurality of receiving elements are serially connected has a tendency for the receiving sensitivity to become smaller. However, with the ultrasonic sensor 1 of this embodiment, even when equipped with a constitution for which a plurality of receiving elements 10 are serially connected, by doing polarization processing of the piezoelectric film 142 and aligning the polarization state, it is possible to prevent the receiving sensitivity from becoming smaller.

Furthermore, because the laminated body of the receiving element 10 is constituted by the thin film type piezoelectric film 142, the lower electrode 141, and the upper electrode 143, compared to when doing polarization processing of a bulk type piezoelectric element, it is possible to perform polarization processing using a lower voltage application.

Second Embodiment

Following, we will describe a second embodiment of the present invention while referring to the drawings.

With the previously described first embodiment, whether or not the piezoelectric film 142 polarization properties are in a stable state or not was determined by measuring the elapsed time after polarization processing of the piezoelectric film 142, but with this embodiment, the difference from the first embodiment is that this is further determined by using receiving signals. Note that with the description below, the same or roughly the same parts that have already been described are given the same code number, and an explanation of those will be omitted.

Figure 6:
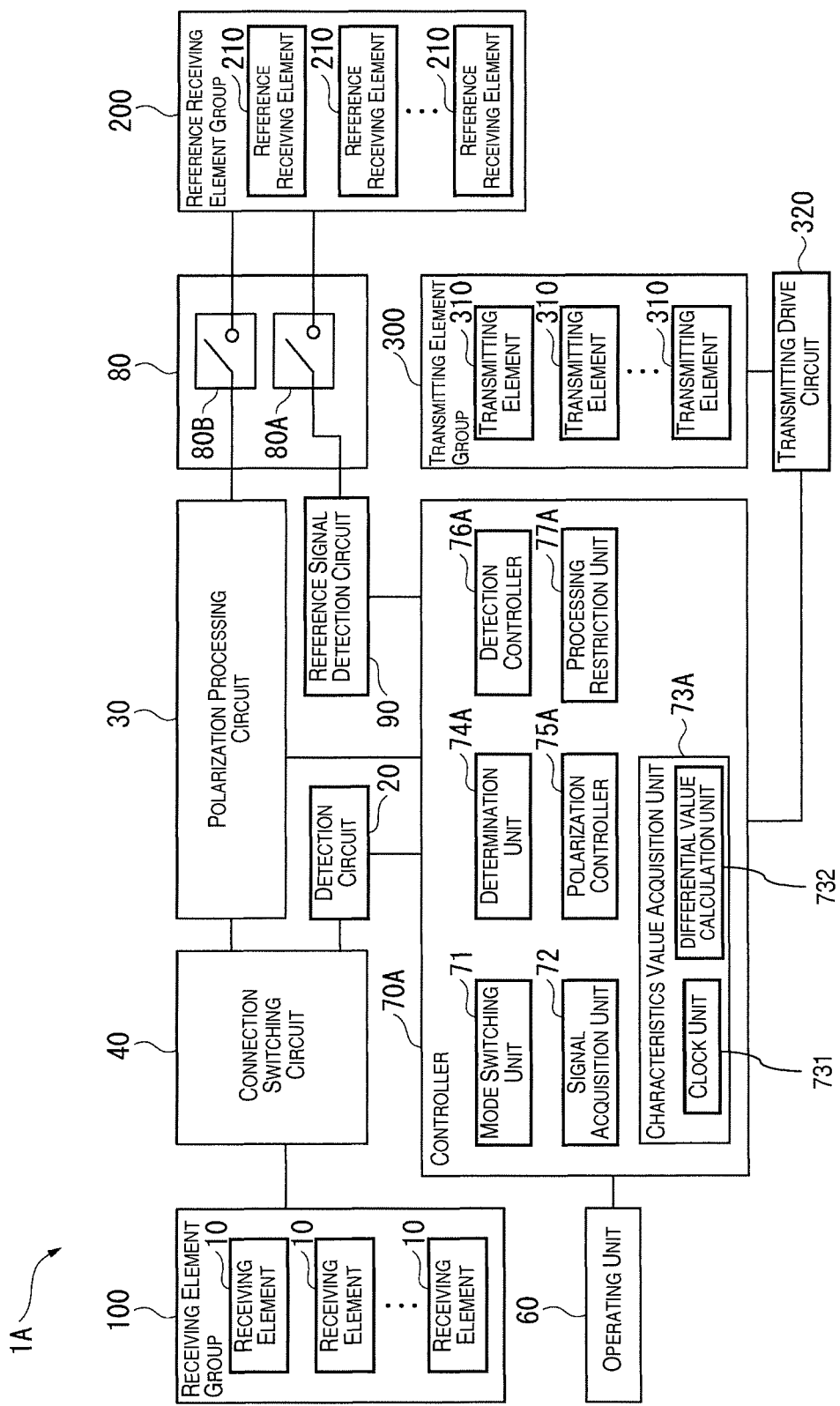
FIG. 6 is a flow chart showing the configuration of the ultrasonic sensor of the second embodiment.

FIG. 6 is a schematic diagram showing the constitution of the ultrasonic sensor 1A of this embodiment.

As shown in FIG. 6, the ultrasonic sensor 1A of this embodiment is equipped with a receiving element group 100, a detection circuit 20, a polarization processing circuit 30, a connection switching circuit 40, an operating unit 60, a transmitting element group 300, a transmitting drive circuit 320, a reference receiving element group 200, a reference connection switching circuit 80 (reference connection switching unit), a reference signal detection circuit 90 (reference signal detection unit), and a controller 70A.

With this ultrasonic sensor 1A, in the signal processing mode for executing normal detection processing, ultrasonic waves are issued from the transmitting element group 300 toward the object to be detected, and by the ultrasonic waves reflected by the object to be detected being received by the receiving element group 100, the distance between the ultrasonic sensor 1A and the object to be detected as well as the state of the object to be detected are detected. Also, in the calibration mode for determining whether or not the polarization state of the receiving element group 100 is a stable state, ultrasonic waves are issued from the transmitting element group 300 toward the reference detection object, and the ultrasonic waves reflected by the reference detection object are received by the receiving element group 100 and the reference receiving element group 200. Then, by comparing the signals respectively output from the receiving element group 100 and the reference receiving element group 200, a determination is made of whether the polarization state of the receiving element group 100 is a stable state or not, and when it is determined to be a stable state, polarization processing is executed.

The transmitting element group 300 is formed by arranging transmitting elements 310 having the same constitution as the receiving elements 10 in an array form. This transmitting element group 300 outputs ultrasonic waves by being connected to the transmitting drive circuit 320, and being driven by the drive signals (pulse voltage) input from the transmitting drive circuit 320. Here, the transmitting element group 300, in contrast to the receiving elements 10 of the receiving element group 100, can be constituted with a plurality of transmitting elements 310 connected in parallel. Also, for example, it is possible to have a constitution with which a plurality of element rows, for which transmitting elements 310 are connected serially along the X axis, are arranged along the Y axis, with these respective element rows individually connected to the transmitting drive circuit 320. Furthermore, it is also possible to constitute this with individual transmitting elements 310 respectively connected individually to the transmitting drive circuit 320.

The reference receiving element group 200 can be constituted with a plurality of the reference receiving elements 210 (reference piezoelectric elements). This reference receiving element 210 is an element used for determining whether the receiving elements 10 are in a stable state or an unstable state.

This reference receiving element 210 is constituted using the same constitutional materials as the receiving element 10, and formed with the same shape and dimensions. Note that the reference receiving element group 200 can also be arranged with the same arrangement and the same connection state as the receiving elements 10 of the receiving element group 100. Also, the reference receiving element 210 can have a different element count from the receiving elements 10.

This reference receiving element group 200 is connected to the reference signal detection circuit 90 and the polarization processing circuit 30 via the reference connection switching circuit 80.

The reference connection switching circuit 80 is equipped with a first reference switch unit 80A provided between the reference receiving element group 200 and the reference signal detection circuit 90, and a second reference switch unit 80B provided between the reference receiving element group 200 and the polarization processing circuit 30. Then, the first reference switch unit 80A switches the connection state between the reference receiving element group 200 and the reference signal detection circuit 90 by the control of the controller 70A. Also, the second reference switch unit 80B switches the connection state between the reference receiving element group 200 and the polarization processing circuit 30 by the control of the controller 70A.

The reference signal detection circuit 90 detects the reference signals output from each reference receiving element 210 in the same manner as the detection circuit 20.

The controller 70A is equipped with the mode switching unit 71, the signal acquisition unit 72, the characteristics value acquisition unit 73A, the determination unit 74A, the polarization controller 75A, the detection controller 76A, and the processing controller 77A.

The characteristics value acquisition unit 73A is equipped with a differential value calculation unit 732 in addition to the previously described clock unit 731.

This differential value calculation unit 732 calculates as the characteristics value the signal differential value of the signal value of the reference signal detected by the reference signal detection circuit 90 subtracted from the signal value of the detection signal detected by the detection circuit 20. Note that when the number of elements differs for the receiving elements 10 and the reference receiving elements 210, it is possible to use as the characteristics value the differential value obtained by subtracting the value for which the signal value of the reference signal detected by the reference receiving element group 200 is divided by the element count of the reference receiving elements 210 from the value for which the signal value of the detection signal detected by the receiving element group 100 is divided by the element count of the receiving elements 10.

The determination unit 74A determines there to be a stability transition state when the elapsed time (t) acquired by the clock unit 731 is the time from immediately after the polarization processing until the first time. Also, when the elapsed time (t) is greater than the second time, the determination unit 74A determines whether the signal differential value calculated by the differential value calculating unit 732 is a prescribed threshold value or less, and when it is the threshold value or less, determines there to be a stable state, and when it is greater than the threshold value, determines there to be an unstable state. For example, as this threshold value, it is possible to set a value for which the margin of error of the detection signals in relation to the reference detection signals is ±10%, and in this case, the determination unit 74A determines this to be a stable state when the characteristics value calculated by the differential value calculation unit 732 is kept within the margin of error range.

When it is determined that the polarization properties of the piezoelectric film 142 are in an unstable state based on the determination results of the determination unit 74A, and the operating mode of the ultrasonic sensor 1 is switched to the calibration mode by the mode switching unit 71, the polarization controller 75A outputs control signals to the connection switching circuit 40, switches the connection state of the connection switching circuit 40 to the second connection state, and has polarization processing of the piezoelectric film 142 performed by the polarization processing circuit 30.

Furthermore, this polarization controller 75A has polarization processing of the reference receiving element 210 done by the polarizing processing circuit 30 with a prescribed timing of the signal processing mode. Note that if this polarization processing of the reference receiving element 210 is done during the signal processing mode, it can be executed with any timing. For example, at the timing when power is supplied by operation of the power switch of the ultrasonic sensor 1A, when the signal processing mode is set as the initial operating mode of the ultrasonic sensor 1A by the mode switching unit 71, it is also possible to do polarization processing of the reference receiving element 210 at the timing immediately after this power supply switch has been operated. Also, after detection processing has been executed by the detection circuit 20, when an input signal to the effect of executing detection processing has not been input from the input means during a prescribed standby transition time, it is also possible to execute polarization processing of the reference receiving element 210. Also, when the power switch is operated to be in an off state, when the detection processing sequence end operation is executed, it is also possible to execute polarization processing of the reference receiving element 210. Furthermore, it is also possible to execute polarization processing of the reference receiving element 210 with any timing by user setting input.

With the polarization processing of the reference receiving element group 200 by the polarization controller 75A, the concerned polarization controller 75A outputs control signals to the reference connection switching circuit 80, and with the first reference switch unit 80A, the reference receiving element group 200 and the reference signal detection circuit 90 are disconnected, and with the second reference switch unit 80B, the connection state is switched to the reference receiving element group 200 and the polarization processing circuit 30 being connected.

When it is determined that the polarization properties of the piezoelectric film 142 are in a stable state based on the determination results of the determination unit 74A, and the operating mode of the ultrasonic sensor 1A is switched to the signal processing mode, the detection controller 76A outputs control signals to the connection switching circuit 40, and switches to the first connection state. Then, the detection signals output from the receiving element group 100 are detected by the detection circuit 20. It is also possible for the detection controller 76A to calculate the distance from the ultrasonic sensor 1A to the object to be detected or the like based on the detected detection signals, or to output the detected detection signals to an external apparatus from an external terminal (not shown), for example.

Then, when the elapsed time (t) acquired by the clock unit 731 is determined to be greater than the second time by the determination unit 74A, the detection controller 76A controls the connection switching circuit 40 and the reference signal detection circuit 90, and temporarily switches to a state for which it is possible for the detection signals from the receiving element group 100 and the reference signals from the reference receiving element group 200 to be detected by the detection circuit 20 and the reference signal detection circuit 90.

When it is determined that the polarization properties of the piezoelectric film 142 are in a stability transition state based on the determination results of the determination unit 74A, and the operating mode of the ultrasonic sensor 1A is switched to the stability transition mode by the mode switching unit 71, the processing restriction unit 77A outputs control signals to the connection switching circuit 40, and switches to the third connection state. Then, the receiving element group 100 is in a state for which the detection circuit 20 and the polarization processing circuit 30 are disconnected.

Operation of Ultrasonic Sensor

Figure 7:
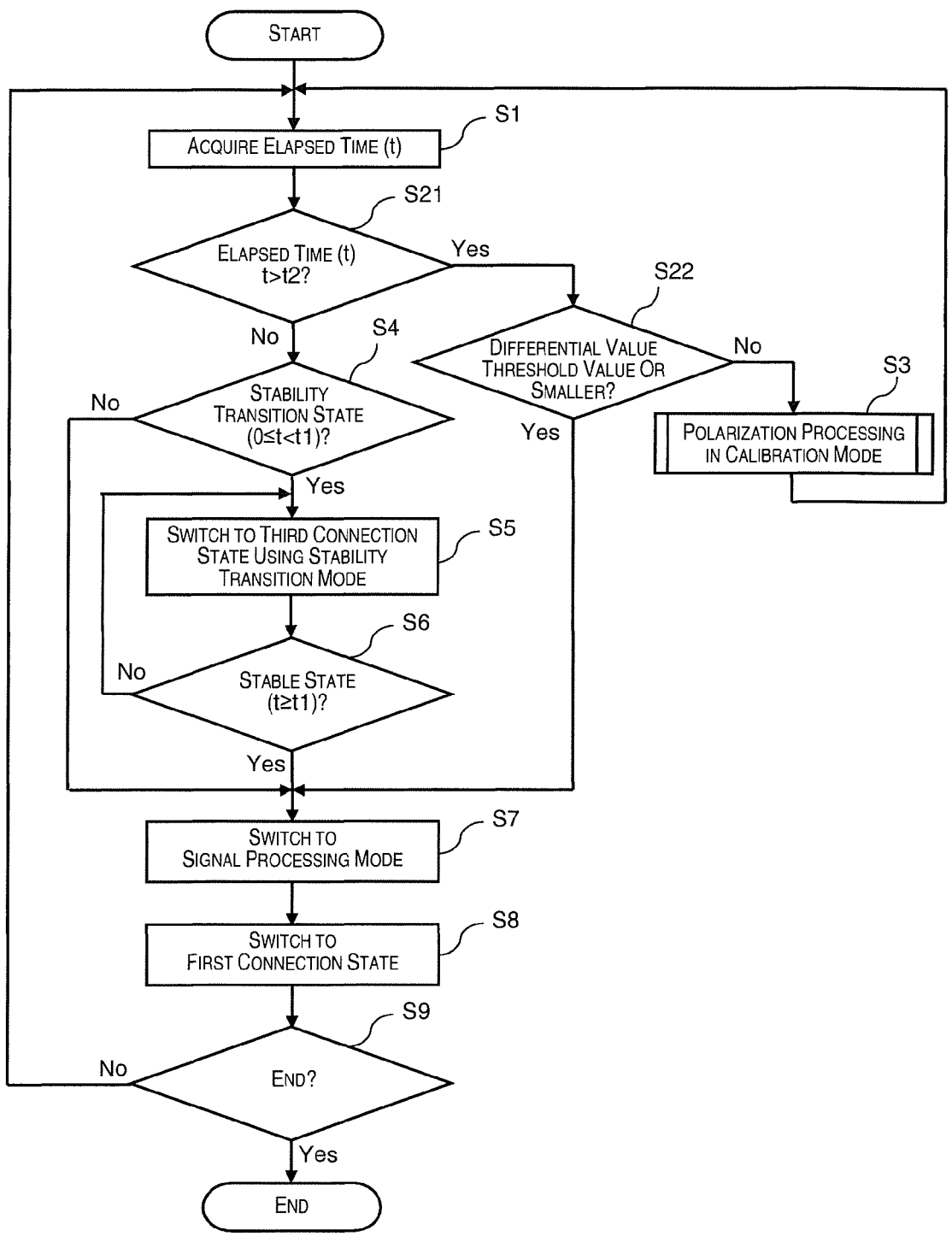
FIG. 7 is a flow chart of the operation of the ultrasonic sensor of the second embodiment.

FIG. 7 is a flow chart showing the operation of the ultrasonic sensor 1A.

With the ultrasonic sensor 1A of this embodiment, after the previously described processing of step S2 of the first embodiment, the determination unit 74A of the controller 70A determines whether or not the elapsed time (t) is greater than the second time t2 (step S21).

When it is determined at step S21 that the elapsed time (t) is the second time t2 or less, the previously described processing from step S4 and therefore is performed. Specifically, the controller 70A uses the determination unit 74A to determine whether the polarization state of each piezoelectric film 142 of the receiving element group 100 is in a stability transition state or in a stable state. Then, when it is determined that this is a stability transition state by the determination unit 74A, the controller 70A has the mode switching unit 71 switch to the stability transition mode, and has the processing restriction unit 77A restrict both processes of the detection circuit 20 and the polarization processing circuit 30 for a prescribed time. Also, when it is determined that this is a stable state by the determination unit 74A, the controller 70A has the mode switching unit 71 switch to the signal processing mode, and sets to a state for which it is possible to do detection processing by the detection circuit 20.

Meanwhile, when it is determined at step S21 that the elapsed time (t) is greater than the second time t2, the differential value calculation unit 732 of the characteristics value acquisition unit 73A acquires the previously described differential value, and determines whether or not the acquired differential value is a threshold value or less (step S22).

In specific terms, at this step S22, the detection controller 76A switches the connection switching circuit 40 to the first connection state, and switches the reference connection switching circuit 80 to the first reference connection state by which the reference receiving element group 200 and the reference signal detection circuit 90 are connected. Also, the controller 70A controls the transmitting drive circuit 320 to issue ultrasonic waves from the transmitting element group 300, and for example receives the ultrasonic waves reflected by the object to be detected at the receiving element group 100 and the reference receiving element group 200. As a result, the detection signals are detected by the detection circuit 20, and the reference signals are detected by the reference signal detection circuit 90.

After that, the differential value calculation unit 732 calculates the differential value (signal differential value) between the acquired receiving signals and the reference signals, and determines whether or not this signal differential value is a threshold value or less.

When it is determined at step S22 that it is the threshold value or lower, the previously described processing from step S7 and thereafter is performed. Specifically, the controller 70A has the operating mode of the ultrasonic sensor 1A switched to the signal processing mode by the mode switching unit 71, and sets to a state for which it is possible to execute detection processing by the detection circuit 20.

Meanwhile, at step S22, when it is determined to be greater than the threshold value, the determination unit 74A determines that there is an unstable state, the previously described polarization processing of step S3 is executed, and after polarization processing, the process returns to step S1.

With the ultrasonic sensor 1A according to the second embodiment described above, in addition to the same effects as the first embodiment being exhibited, the following effects are also exhibited.

The ultrasonic sensor 1A is equipped with the detection circuit 20 for detecting detection signals output from the receiving elements 10, the reference receiving elements 210 constituted with the same constitutional materials and formed in the same shape and dimensions as the receiving elements 10, which output reference signals according to received ultrasonic waves by receiving ultrasonic waves, and the reference signal detection circuit 90 for detecting reference signals output from the reference receiving elements 210. Then, the characteristics value acquisition unit 73A of the controller 70A calculates as the characteristics value the differential value of this detected signal and the reference signal, and the determination unit 74A determines there to be a stable state when this calculated differential value is a prescribed threshold value or less, and determines there to be an unstable state when the differential value is greater than the threshold value.

Because of this, it is possible to make a quantitative judgment of the decrease volume of the receiving sensitivity of the receiving elements 10 based on reference signals from the reference receiving elements 210 and the detection signals from the receiving element 10. Therefore, because it is possible to more accurately judge the polarization state of the receiving elements 10, it is possible to do polarization processing of the piezoelectric film 142 of each receiving element 10 at more optimal timing.

Also, with the ultrasonic sensor 11A of this embodiment, the polarization controller 75A has the polarization processing of the reference receiving elements 210 done by the polarization processing circuit 30 in the signal processing mode. Because of this, the reference receiving elements 210 are able to determine the polarization state of the receiving elements 10 accurately since the polarization direction of each piezoelectric film 142 are in an aligned state in the calibration mode.

Modification Examples

Note that the present invention is not restricted to the embodiments described above, and the present invention includes variations and improvements within a scope that can achieve the objects of the present invention.

With the second embodiment noted above, a determination of whether or not this is in an unstable state was made when the elapsed time (t) was greater than the second time t2 using the signal differential value, but the invention is not limited thereto. For example, it is also possible to determine whether in a stability transition state, or whether in an unstable state with t≤t2 as well using the signal differential value. In specific terms, during the period when the elapsed time (t) is 0≤t≤t1, when the signal differential value exceeds the stability upper limit value, this is determined to be in a stability transition state, and if the signal differential value is within the threshold range from the stability upper limit value to the stability lower limit value, it is also possible to switch the operating mode to the signal processing mode and do processing. In this case, when the polarization state of the piezoelectric film 142 goes to a stable state more quickly than normal, it is possible to switch to the signal processing mode more quickly in accordance with this, making it possible to execute detection work quickly. Also, with t1≤t≤t2 as well, for example when periodically doing comparison processing of the signals of the reference receiving element group 200 and the receiving element group 100, and the signal differential value is between the stability upper limit value and the stability lower limit value, this can be determined to be the stability transition state or the unstable state. In other words, even if the polarization state of the piezoelectric film 142 is unaligned, and the receiving sensitivity decreases, it is possible to determine the polarization state of the piezoelectric film 142 quickly, so it is possible to quickly restore the performance by executing polarization processing, and to prevent a decrease in detection precision.

With each of the embodiments noted above, we showed examples of the receiving elements 10 for receiving ultrasonic waves as the piezoelectric element for performing polarization processing, but the invention is not limited to this, and it is also possible to have a constitution for which polarization processing is done for transmitting elements that transmit ultrasonic waves, or to use a constitution for which polarization processing is performed for both receiving elements 10 and transmitting elements. When using a constitution for performing polarization processing for transmitting elements, it is possible to constitute this equipped with transmitting elements for transmitting ultrasonic waves, and a drive circuit for performing drive processing to drive those elements.

Note that when using the constitution for doing polarization processing of the transmitting elements with the second embodiment, reference transmitting elements for issuing ultrasonic waves of a reference sound pressure and a reference transmitting drive circuit for driving those elements are provided, and the ultrasonic waves output from the reference transmitting elements and the ultrasonic waves output from the transmitting elements are received by one receiving element. Then, the receiving signal value of the ultrasonic waves based on the reference transmitting element and the receiving signal value of the ultrasonic waves based on the transmitting element are compared, and if the margin of error is outside a threshold range, polarization processing of the transmitting element is done. As a result, it is possible to always maintain a suitable polarization processed state for the transmitting elements.

With each of the embodiments noted above, examples were shown of a constitution by which the plurality of receiving elements 10 are serially connected, but it is also possible to have the number of receiving elements be singular (single element), and to have a constitution for which a plurality of receiving elements 10 are connected in parallel.

With each of the embodiments noted above, as the piezoelectric element, we described receiving elements 10 equipped with a laminated body 14 constituted with a thin film type piezoelectric film 142, lower electrode 141, and upper electrode 143, but the piezoelectric element can also be a bulk type.

With each of the embodiments noted above, we showed examples regarding a constitution for performing polarization processing of the piezoelectric film 142 and performing detection by the detection circuit 20 after polarization processing when it is determined that the piezoelectric properties of the piezoelectric film are no longer in a stable state, but it is also possible to use a constitution for which a determination of the useable state of the piezoelectric film 142 is made based on the detection results or the like of that detection circuit 20, and to perform processing according to the determination results.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A piezoelectric sensor device comprising:
   a piezoelectric element having a piezoelectric body and a pair of electrodes sandwiching the piezoelectric body;
   a polarization processing unit configured to execute polarization processing in which polarization voltage is applied to the piezoelectric element; and
   a controller configured to control an execution timing of the polarization processing by the polarization processing unit, the controller including
      a characteristics value acquisition unit configured to acquire a characteristics value relating to a polarization volume of the piezoelectric body,
      a determination unit configured to determine whether a polarization property of the piezoelectric body is in a stable state or in an unstable state based on the characteristics value, and
      a polarization controller configured to control the polarization processing unit to apply the polarization voltage to the piezoelectric body when the determination unit determines that the polarization property of the piezoelectric body is in the unstable state.

2. The piezoelectric sensor device according to claim 1, wherein
   the characteristics value acquisition unit includes a clock unit configured to acquire as the characteristics value an elapsed time from an execution timing of the polarization processing by the polarization processing unit, and
   the determination unit is configured to determine that the polarization property of the piezoelectric body is in the stable state when the elapsed time falls between a first time and a second time, over which the polarization property of the piezoelectric body stabilizes, and to determine that the polarization property of the piezoelectric body is in the unstable state when the elapsed time is greater than the second time.

3. The piezoelectric sensor device according to claim 2, further comprising
   a signal processing unit configured to execute at least one of detection processing for detecting a detection signal output from the piezoelectric element and drive processing for inputting a drive signal to the piezoelectric element to drive the piezoelectric element,
   the controller being configured to stop the polarization processing of the piezoelectric body by the polarization processing unit and signal processing by the signal processing unit when the elapsed time is smaller than the first time.

4. The piezoelectric sensor device according to claim 3, wherein
   the piezoelectric element is configured to output a detection signal according to received ultrasonic waves, and
   the piezoelectric sensor device further comprises
      a signal processing unit configured to detect a detection signal output from the piezoelectric element;
      a reference piezoelectric element constituted using the same structural materials as the piezoelectric element and formed with the same shape and dimensions thereof, and configured to output a reference signal according to the received ultrasonic waves; and
      a reference signal detection unit configured to detect the reference signal output from the reference piezoelectric element,
   the characteristics value acquisition unit includes a differential value calculating unit configured to calculate as the characteristics value a differential value between the detection signal detected by the signal processing unit and the reference signal detected by the reference signal detection unit, and
   the determination unit is configured to determine that the polarization property of the piezoelectric body is in the stable state when the differential value calculated by the differential value calculating unit is a prescribed threshold or less, and to determine that polarization property of the piezoelectric body is in the unstable state when the differential value is greater than the prescribed threshold.

5. The piezoelectric sensor device according to claim 4, further comprising
   a mode switching unit configured to switch between a signal processing mode in which at least one of signal transmission processing and signal receiving processing of ultrasonic waves from the piezoelectric element is executed, and a calibration mode in which the polarization processing of the piezoelectric element is executed,
   the polarization controller is configured to control the polarization processing unit to execute the polarization processing of the reference piezoelectric element in the signal processing mode.

6. The piezoelectric sensor device according to claim 2, wherein
  the piezoelectric element is configured to output a detection signal according to received ultrasonic waves, and
  the piezoelectric sensor device further comprises
    a signal processing unit configured to detect a detection signal output from the piezoelectric element;
    a reference piezoelectric element constituted using the same structural materials as the piezoelectric element and formed with the same shape and dimensions thereof, and configured to output a reference signal according to the received ultrasonic waves; and
    a reference signal detection unit configured to detect the reference signal output from the reference piezoelectric element,
  the characteristics value acquisition unit includes a differential value calculating unit configured to calculate as the characteristics value a differential value between the detection signal detected by the signal processing unit and the reference signal detected by the reference signal detection unit, and
  the determination unit is configured to determine that the polarization property of the piezoelectric body is in the stable state when the differential value calculated by the differential value calculating unit is a prescribed threshold or less, and to determine that polarization property of the piezoelectric body is in the unstable state when the differential value is greater than the prescribed threshold.

7. The piezoelectric sensor device according to claim 6, further comprising
  a mode switching unit configured to switch between a signal processing mode in which at least one of signal transmission processing and signal receiving processing of ultrasonic waves from the piezoelectric element is executed, and a calibration mode in which the polarization processing of the piezoelectric element is executed,
  the polarization controller is configured to control the polarization processing unit to execute the polarization processing of the reference piezoelectric element in the signal processing mode.

8. The piezoelectric sensor device according to claim 1, wherein
  the piezoelectric element is configured to output a detection signal according to received ultrasonic waves, and
  the piezoelectric sensor device further comprises
    a signal processing unit configured to detect a detection signal output from the piezoelectric element;
    a reference piezoelectric element constituted using the same structural materials as the piezoelectric element and formed with the same shape and dimensions thereof, and configured to output a reference signal according to the received ultrasonic waves; and
    a reference signal detection unit configured to detect the reference signal output from the reference piezoelectric element,
  the characteristics value acquisition unit includes a differential value calculating unit configured to calculate as the characteristics value a differential value between the detection signal detected by the signal processing unit and the reference signal detected by the reference signal detection unit, and
  the determination unit is configured to determine that the polarization property of the piezoelectric body is in the stable state when the differential value calculated by the differential value calculating unit is a prescribed threshold or less, and to determine that polarization property of the piezoelectric body is in the unstable state when the differential value is greater than the prescribed threshold.

9. The piezoelectric sensor device according to claim 8, further comprising
  a mode switching unit configured to switch between a signal processing mode in which at least one of signal transmission processing and signal receiving processing of ultrasonic waves from the piezoelectric element is executed, and a calibration mode in which the polarization processing of the piezoelectric element is executed,
  the polarization controller is configured to control the polarization processing unit to execute the polarization processing of the reference piezoelectric element in the signal processing mode.

10. A polarization method of a piezoelectric body of a piezoelectric sensor device including a piezoelectric element having a piezoelectric body and a pair of electrodes sandwiching the piezoelectric body, and a polarization processing unit configured to execute polarization processing in which polarizing voltage is applied to the piezoelectric element, the polarization method comprising:
  acquiring a characteristics value relating to a polarization volume of the piezoelectric body;
  determining whether a polarization property of the piezoelectric body is in a stable state or in an unstable state based on the characteristics value; and
  controlling the polarization processing unit to execute the polarization processing of the piezoelectric body when the polarization property of the piezoelectric body is determined to be in the unstable state.

11. The polarization method of a piezoelectric body of a piezoelectric sensor device according to claim 10, wherein
  the characteristics value is an elapsed time from an execution timing of the polarization processing by the polarization processing unit.

* * * * *